United States Patent [19]

Robey et al.

[11] 4,318,866

[45] Mar. 9, 1982

[54] CHLORINATION OF 4-METHOXYBENZOYL CHLORIDE

[75] Inventors: Roger L. Robey, Greenwood; Jeffrey C. Smirz, Indianapolis, both of Ind.

[73] Assignee: Eli Lilly and Company, Indianapolis, Ind.

[21] Appl. No.: 139,050

[22] Filed: Apr. 10, 1980

[51] Int. Cl.$^3$ .............................................. C07C 65/21
[52] U.S. Cl. .................................................. 260/544 D
[58] Field of Search ...................................... 260/544 D

[56] References Cited

U.S. PATENT DOCUMENTS 3,935,258  1/1976  Hempel et al. ..................... 564/48

OTHER PUBLICATIONS

Louw, Robert et al. *Chemistry and Industry*, Feb. 1977, pp. 127–128.
Yagupol'skii, L. M. *Chemical Abstracts*, vol. 50 (1956) #11270a.
Yagupol'skii, L. M. et al. *Chemical Abstracts*, vol. 51 (1957) #15518c.

*Primary Examiner*—Nicky Chan
*Assistant Examiner*—L. Hendriksen
*Attorney, Agent, or Firm*—Joseph A. Jones; Arthur R. Whale

[57] ABSTRACT

An improved process for chlorinating 4-methoxybenzoyl chloride on the methyl group with molecular chlorine is done neat at elevated temperature in the absence of light of radical-forming intensity.

4 Claims, No Drawings

CHLORINATION OF 4-METHOXYBENZOYL CHLORIDE

BACKGROUND OF THE INVENTION

1. Field of the Invention

This invention provides a convenient method for preparing 4-trichloromethoxybenzoyl chloride by the direct chlorination of 4-methoxybenzoyl chloride, without the use of either a chlorination catalyst or radical initiators. The product is useful as an intermediate for the synthesis of other organic compounds.

2. State of the Art

L. M. Yagupol'skii, *Doklady Akad. Nauk S.S.S.R.* 105, 100–102 (1955) taught the synthesis of 4-trichloromethoxybenzoyl chloride by the chlorination in the presence of phosphorus pentachloride of 4-methoxybenzoyl chloride. The same compound was also prepared by Hempel and Klauke, U.S. Pat. No. 3,935,258, using chlorination in the presence of a radical-forming agent, such as ultraviolet light or a peroxide.

An article by Louw and Franken, *Chem. and Ind.* 127 (Feb. 5, 1977) is also important to the background of this invention. The article shows that chlorination of methoxybenzene gives predominately ring-chlorination, not side-chain chlorination, but that methoxybenzene is chlorinated on the methoxy group with the assistance of ultraviolet light to create free-radical conditions.

SUMMARY OF THE INVENTION

This invention provides an improved process for preparing 4-trichloromethoxybenzoyl chloride by chlorinating 4-methoxybenzoyl chloride with molecular chlorine at elevated temperature, wherein the improvement comprises carrying out the reaction neat in the absence of light of radical-forming intensity at from about 150° C. to about 225° C.

DESCRIPTION OF THE PREFERRED EMBODIMENTS

As has been explained, the art has used direct chlorination to prepare the subject compound, but it has hitherto been believed necessary to use either a chlorination catalyst, usually phosphorus pentachloride, or free radical initiators, especially strong ultraviolet light.

The use of light as an initiator is expensive and inconvenient because of the power needed to generate the strong light intensity. It has been found that phosphorus pentachloride is also disadvantageous, because it tends to plug the condenser of the reactor. The present invention avoids the disadvantages of the prior processes.

The process of this invention is carried out at an elevated temperature in the range of from about 150° C. to about 225° C. It is preferred to operate at temperatures from about 170° C. to about 210° C., and it is most preferred to begin the chlorination at a temperature in the range of from about 150° C. to about 170° C., and to raise the temperature gradually or step-wise until the maximum temperature, near the upper end of the ranges just discussed, is reached near the end of the process.

The process of this invention is carried out neat, that is, in the absence of solvents, catalysts or diluents. The starting compound is placed in an appropriate reactor, equipped with heating facilities and an agitator. It is heated to the desired temperature as discussed above, and molecular chlorine is bubbled through it with mixing at an addition rate such that the chlorine is consumed efficiently by the reaction.

The reaction may be carried out at ambient pressure, or at elevated pressure. The use of elevated pressure can increase the utilization of the chlorine, and increase the speed of the reaction as well.

Some excess chlorine is used, if an essentially complete conversion of the starting compound is desired. The chlorination of each mole of starting compound consumes 3 moles of chlorine, producing one mole of product and 3 moles of hydrogen chloride gas. It appears that the chlorination proceeds step-wise, and that at least some of the desired product is obtained soon after the chlorination begins. Thus, the amount of excess chlorine is not a critical limitation, since some of the desired product will be obtained even when less than the theoretical amount of chlorine is added. For best operation, however, from about 20% to about 100% excess chlorine should be used.

The rate of addition of the chlorine to the starting compound depends upon the speed of reaction and upon the state of mixing in the reactor. Accordingly, operation at higher temperatures increases the reaction rate and the rate at which chlorine may be added. Operation of the process in a vessel designed for efficient mixing also increases the rate at which chlorine may be added. In general, however, the total time during which chlorine is added is in the range of from about 3 to about 12 hours, if the reaction is carried out in such a way as to use the chlorine efficiently and to obtain essentially complete conversion of the starting compound.

The only waste product of the reaction is hydrogen chloride, which leaves the reaction mixture as a gas, mixed with chlorine which has not reacted. It will be understood that the off-gas should be caught, rather than vented to the atmosphere, and that it can be scrubbed in a conventional vapor scrubber, using, for example, sodium hydroxide solution as the scrubber liquid. Recovery of the lost chlorine will be more complete if a reducing agent such as sodium thiosulfate or bisulfite is included in the scrubber liquid.

The starting compound used in this process is known in the organic chemical literature. The product of the process is an intermediate compound, which is converted to 4-trifluoromethoxybenzoyl fluoride by reaction with antimony pentafluoride or with hydrogen fluoride. That compound is then converted to 4-trifluoromethoxybenzamide with ammonium hydroxide, and then to 4-trifluoromethoxybenzonitrile with phosphorus oxychloride. Finally, the benzonitrile is reacted with isopropyl magnesium chloride or bromide to prepare isopropyl 4-trifluoromethoxyphenyl ketone, which is used to prepare fungicides and plant growth regulators according to the process of U.S. Pat. No. 4,110,099. An example showing each step of the use of the compound prepared according to this invention is provided below.

The following examples illustrate the process of this invention. The product of each of the experiments was analyzed by vapor-phase chromatography, by comparison with a standard sample of 4-trichloromethoxybenzoyl chloride, having the following nuclear magnetic resonance characteristic peaks:

$\delta(CDCl_3)$: 7.35–8.30 (4H, quartet centered at 7.82 $\delta$).

The chromatography was performed on a 1.85 meter column, 2 mm. in diameter, packed with 3% SE-30 on Varaport-30 support, at a helium flow of 25 ml./min.

EXAMPLE 1

An 85.3 g. portion of 4-methoxybenzoyl chloride was added to a 250 ml. 3-necked flask. The flask was connected to a scrubber filled with 4 liters of 5% sodium hydroxide solution. The reaction flask was heated to 225° C., and chlorine was added through a sparging tube at the rate of about 25 g./hour while the temperature of the reaction mixture was held constant. A total of 184 g. of chlorine was added over 7½ hours. The reaction mixture was then cooled, and was analyzed by vapor-phase chromatography. The yield was 127.9 g. of crude product, analyzing 83.8% pure. The yield was 78% of the theoretical yield.

EXAMPLE 2

The apparatus of Example 1 was used again. In this experiment, the addition of chlorine was started at a reactor temperature of 150° C., and continued at constant temperature for 3.5 hours. The temperature was then raised to 180° C. for 3.5 hours more, and then to 210° C. for 3 hours more. A total of 239 g. of chlorine was added over a period of 10 hours. The yield was 131 g. of crude product, analyzing 85.5% pure, a yield of 82% of theoretical.

EXAMPLE 3

The apparatus of Example 1 was used again; in this experiment, the scrubber solution was 4 liters of 2.75% sodium hydroxide solution containing 1.4% of sodium bisulfite. The starting compound was heated to 170°-175° C. The addition of chlorine was then started, and was continued at constant temperature for 4.5 hours. The temperature was then raised to 185°-190° C., and was held at that temperature for about 4 hours, while chlorine was added at a constant rate. Finally, the temperature was raised to 200°-205° C., for the final 2.8 hours of the process. A total of 135.1 g. of chlorine was added over the 11.3 hour period of the run. The product was cooled and found to weigh 133.1 g., and analyzed 91% pure. The yield was 88.6% of the theoretical yield.

EXAMPLE 4

Fifty-six kg. of 4-methoxybenzoyl chloride (analyzing 99% plus pure) was charged to a 120-liter glass-lined still equipped with a heating jacket, a sparging tube and an agitator. The still was also equipped with a condenser and a vapor scrubber. The starting compound was warmed to 160° C., and chlorine was added at about 150 g./minute. The reaction mixture was warmed to 200° C. and the temperature was held constant. After about 5 hours of operation, it was necessary to shut the process down for the night. The mixture was reheated the following day and the addition of chlorine continued at 200° C. The reaction mixture was allowed to cool overnight again, was reheated on the third day and the addition of chlorine was continued at the same temperature. At the end of the third day the process was shut down for the weekend, and was then reheated and chlorine was added until the reaction appeared to be complete. A total of 127 kg. of chlorine was added over a total operating time of 17.25 hours. The operating time was prolonged because mechanical difficulties made the chlorine addition rate unnecessarily slow. The crude product amounted to 85 kg., analyzing 94% pure, giving a yield of 89% of theoretical.

EXAMPLE 5

To a 750-liter still, similar to that described in Example 4, was added 270 kg. of 4-methoxybenzoyl chloride. The starting compound was heated to 170° C., and the addition of chlorine was started. It was found that the chlorine addition rate was only 150-400 g./minute, because of deficiencies in the addition system. Accordingly the reaction took approximately 100 hours to complete, counting periods of down time necessary to change chlorine cylinders and take care of occasional problems in the scrubber system.

When approximately ¼ of the estimated amount of chlorine had been added, the temperature was raised to 180°-185° C., and held at that temperature while the second fourth of the chlorine was added. The temperature was then raised to 200°-205° C. until about 90% of the chlorine had been added, and the reaction mixture was then heated to 210° C. for the end of the reaction period. A total of 596 kg. of chlorine was added, amounting to 76% excess chlorine. It was found that the extremely long reaction time at temperature resulted in an apparent inhibition of the reaction, resulting in inefficient use of chlorine.

The product was 418.5 kg., analyzing 84% pure, giving a yield of 81% of the theoretical yield.

Preparation 1

4-Trifluoromethoxybenzoyl fluoride

A 1-liter autoclave was precooled to −20° C., and was charged with 263 g. of 4-trichloromethoxybenzoyl chloride and 300 g. of hydrogen fluoride. The autoclave was sealed and heated to 140° C. for 5 hours. The maximum pressure was 52 kg./sq. cm. soon after reaching temperature, and 21 kg./sq. cm. 3 hours thereafter. The reaction mixture was then cooled to 60° C. over 1 hour, and cooled to ambient temperature overnight. The yield was 319 g. of reaction mixture, containing excess hydrogen fluoride.

Preparation 2

4-Trifluoromethoxybenzamide

The product of Preparation 1 was added to 800 ml. of 28% ammonium hydroxide, in an ice-salt bath. The time of addition was 30 minutes, and the final temperature was 40° C. The mixture was filtered, and the solids were washed with water and dried at 80° C. under vacuum to provide 179 g. of product, m.p. 125°-138° C.

Preparation 3

4-Trifluoromethoxybenzonitrile

A 10.26 g. portion of 4-trifluoromethoxybenzamide was added to 30 ml. of toluene, and heated to 100° C. under nitrogen with stirring. A 4.6 g. portion of phosphorus oxychloride dissolved in 8 ml. of toluene was added dropwise over a period of 30 minutes, and the mixture was stirred under reflux for 1 hour after the addition. The mixture was then cooled, and was distilled under vacuum. After the solvent came off, 8.36 g. of the desired product, b.p. 89° C. at 45 mm. mercury, was obtained from the distillation.

Preparation 4

Isopropyl 4-trifluoromethoxyphenyl ketone

A 10 g. portion of 4-trifluoromethoxybenzonitrile was added to 50 ml. of toluene, and the mixture was stirred at 20° C. while 24 ml. of 2.85-molar isopropyl magnesium bromide solution in diethyl ether was added dropwise over 5 minutes. The mixture was then heated to 55° C. for 4 hours. The mixture was then cooled to ambient temperature, and was poured over ice-hydrochloric acid. The aqueous mixture was then distilled until the temperature rose to 90° C., and was then stirred under reflux for 30 minutes and cooled. The layers were separated, and the aqueous layer was extracted 3 times with 25 ml. portions of dichloromethane. The combined organic layers were dried over sodium sulfate, and the solvent was removed. The residue was then distilled, and the product was collected at 22 mm. mercury and 115°–117° C. The yield was 10.9 g. of the desired product.

The product of Preparation 4 is used to prepare α-isopropyl-α-(4-trifluoromethoxyphenyl)-5-pyrimidinemethanol as taught in U.S. Pat. No. 4,110,099.

We claim:

1. An improved process for preparing 4-trichloromethoxybenzoyl chloride by chlorinating 4-methoxybenzoyl chloride with molecular chlorine at elevated temperature, wherein the improvement consists of carrying out the reaction neat in the absence of light of radical-forming intensity at from about 150° C. to about 225° C.

2. A process of claim 1 wherein the temperature is from about 170° C. to about 210° C.

3. A process of claim 2 wherein the reaction time is from about 3 to about 12 hours.

4. A process of claim 3 wherein the temperature is about 170° C. at the beginning of the chlorination and the temperature is increased gradually or step-wise until the temperature is about 210° C. near the end of the process.

* * * * *